(12) United States Patent
Kondo et al.

(10) Patent No.: US 6,217,605 B1
(45) Date of Patent: Apr. 17, 2001

(54) ARM DEVICE FOR RETAINING AND POSITIONING AN OPTICAL FIBER UNIT FOR MEDICAL EXAMINATION

(75) Inventors: Hiroaki Kondo, Kanagawa; Takemi Kobayashi, Tokyo, both of (JP)

(73) Assignee: Tokyo Iken Co., Ltd., Tokyo (JP)

( * ) Notice: Subject to any disclaimer, the term of this patent is extended or adjusted under 35 U.S.C. 154(b) by 0 days.

(21) Appl. No.: 09/255,952

(22) Filed: Feb. 23, 1999

Related U.S. Application Data

(62) Division of application No. 08/987,031, filed on Dec. 9, 1997.

(30) Foreign Application Priority Data

Dec. 9, 1996 (JP) .................................................. 8-344591

(51) Int. Cl.[7] .................................................. A61N 5/00
(52) U.S. Cl. .................................. 607/88; 607/90; 607/93; 606/16
(58) Field of Search .................. 606/1, 2, 10, 13–16, 606/18, 19; 269/45, 75; 607/88, 89, 90, 93; 433/29–31

(56) References Cited

U.S. PATENT DOCUMENTS

| 4,253,649 | * | 3/1981 | Hewson | 269/45 |
| 4,461,282 | * | 7/1984 | Ouchi et al. . | |
| 4,473,074 | * | 9/1984 | Vassiliadis | 606/19 |
| 5,568,503 | * | 10/1996 | Omori | 606/16 |

FOREIGN PATENT DOCUMENTS 6-27172    7/1994    (JP) .

* cited by examiner

*Primary Examiner*—Michael Peffley
*Assistant Examiner*—Bryan K. Yarnell
(74) *Attorney, Agent, or Firm*—Ostrolenk, Faber, Gerb & Soffen, LLP

(57) ABSTRACT

An arm device for retaining and positioning an optical fiber unit for medical examination and treatment, so as to easily operate the same. The arm device is provided with flexible arm parts and a lockable, rotatable joint assembly for easy manipulation and positioning of the optical fiber unit.

3 Claims, 9 Drawing Sheets

ARM DEVICE FOR RETAINING AND POSITIONING AN OPTICAL FIBER UNIT FOR MEDICAL EXAMINATION

This is a division of application Ser. No. 08/987,031, filed Dec. 9, 1997, which is pending.

BACKGROUND OF THE INVENTION AND RELATED ART STATEMENT

The present invention relates to an optical fiber unit for medical examination and treatment and arm device for the optical fiber, and in particular relates to an optical fiber unit for medical examination and treatment, which is able to cure and treat an affected part by a heating effect, etc. by irradiating infrared rays to the affected part and an arm device for the optical fiber, which is able to retain the optical fiber unit so as to easily operate the same.

Conventionally, this kind of optical fiber unit for medical examination and treatment was such that, like an optical fiber unit for medical examination and treatment disclosed, for example, in Japanese Utility Model Publication No. 27172 of 1994, light including infrared rays, which was emitted from a light source, was guided through an optical fiber light guide, was condensed by a light condensing lens group and irradiated onto an affected part.

Furthermore, a conventional arm device for optical fibers is formed so that the two arm parts thereof are formed of two or three joint parts, and when an optical fiber unit to which the arm device is attached is operated, the arm device flexes or turns, following the operation thereof, thereby causing the operation of the optical fiber unit to be improved.

Since the abovementioned optical fiber unit for medical examination and treatment was constructed so that infrared rays emitted from a light source were guided through a fiber light guide, condensed by a light condensing lens group and irradiated onto an affected part, a light condensing lens group which is precision as an optical component was an indispensable factor, there was such a problem, where the production cost was increased, and the assembling thereof was not made easy.

Furthermore, with the conventional arm device for optical fibers, since the two arm parts had a fixed length, there were still further problems, where they were short of flexibility, did not adapt themselves to the operating environments, an excessive load is applied to the joint parts due to the gravity when the arm part was elongated in the horizontal direction, wherein the posture thereof could not be kept constant.

OBJECTS AND SUMMARY OF THE INVENTION

In view of the abovementioned points, it is therefore an object of the invention to provide an optical fiber unit for medical examination and treatment in which no light condensing lens group is required by making the tip end part of optical fiber light guide a tapered conduit part, the diameter of which is gradually made smaller toward the tip end thereof.

Another object of the invention is to provide an arm device for optical fiber, which by being provided with extendable arm parts and a joint part which can be locked in one direction, is able to adapt itself to the operating environments of the optical fiber unit and to keep the posture thereof constant with the arm parts thereof elongated in the horizontal direction.

An optical fiber unit for medical examination and treatment according to the invention, which treats and cures an affected part by irradiating light including infrared rays emitted from a light source onto the affected part through a flexible optical fiber light guide is characterized in that the tip end side of the optical fiber light guide consists of a tapered conduit part, the diameter of which is made smaller toward the top end thereof, the tapered conduit part condenses light including the infrared rays and irradiates the same to the affected part.

According to an optical fiber unit for medical examination and treatment of the invention, since the tip end part of the optical fiber light guide is made a tapered conduit part and no light condensing lens group is required, there are effects by which the production cost of the device can be decreased by elimination of expensive optical components, and the assembling thereof can be made easier.

Furthermore, an arm device for optical fiber according to the invention is characterized in having a base part fixed at the light source main body, a first joint part rotatably centering around the shaft of the base part and is attached so as to be rockable in one direction via a one-way clutch in the perpendicular plane with respect to the rotating plane, a first extendable arm part attached to the first joint part, a second joint part rotatably centering around the shaft of the first extendable arm part and is attached so as to be rockable in one direction via a one-way clutch in the perpendicular plane with respect to the rotating plane, a second extendable arm part attached at the second joint part, a third joint part rotatably and rockably attached to the second extendable arm part, and a probe retaining part for retaining a probe of an optical fiber unit attached to the third joint part.

Since an arm device for optical fiber according to the invention is provided with two extendable arm parts, two joint parts having a one-way clutch, and one joint part having a universal joint, it is possible to move the probe so as to adapt the arm device to the operating environments of an optical fiber unit, and simultaneously the posture of the arm device can be kept constant even though the arm part is elongated in the horizontal direction, whereby there is an effect of remarkably increasing the operation efficiency of the optical fiber unit.

Furthermore, since the first joint part is provided with an operating member for cancelling the locking of one-way clutch, there is an effect by which the movement of the first extendable arm part toward any optional inclined position can be further facilitated.

Still furthermore, since the second joint part is provided with a guiding part for insertably nipping a flexible guide tube of the optical fiber unit therebetween, there is an effect by which the followability of the arm device for optical fiber to the optical fiber unit can be further improved.

DETAILED DESCRIPTION OF THE PREFERRED EMBODIMENTS

Figure 1:
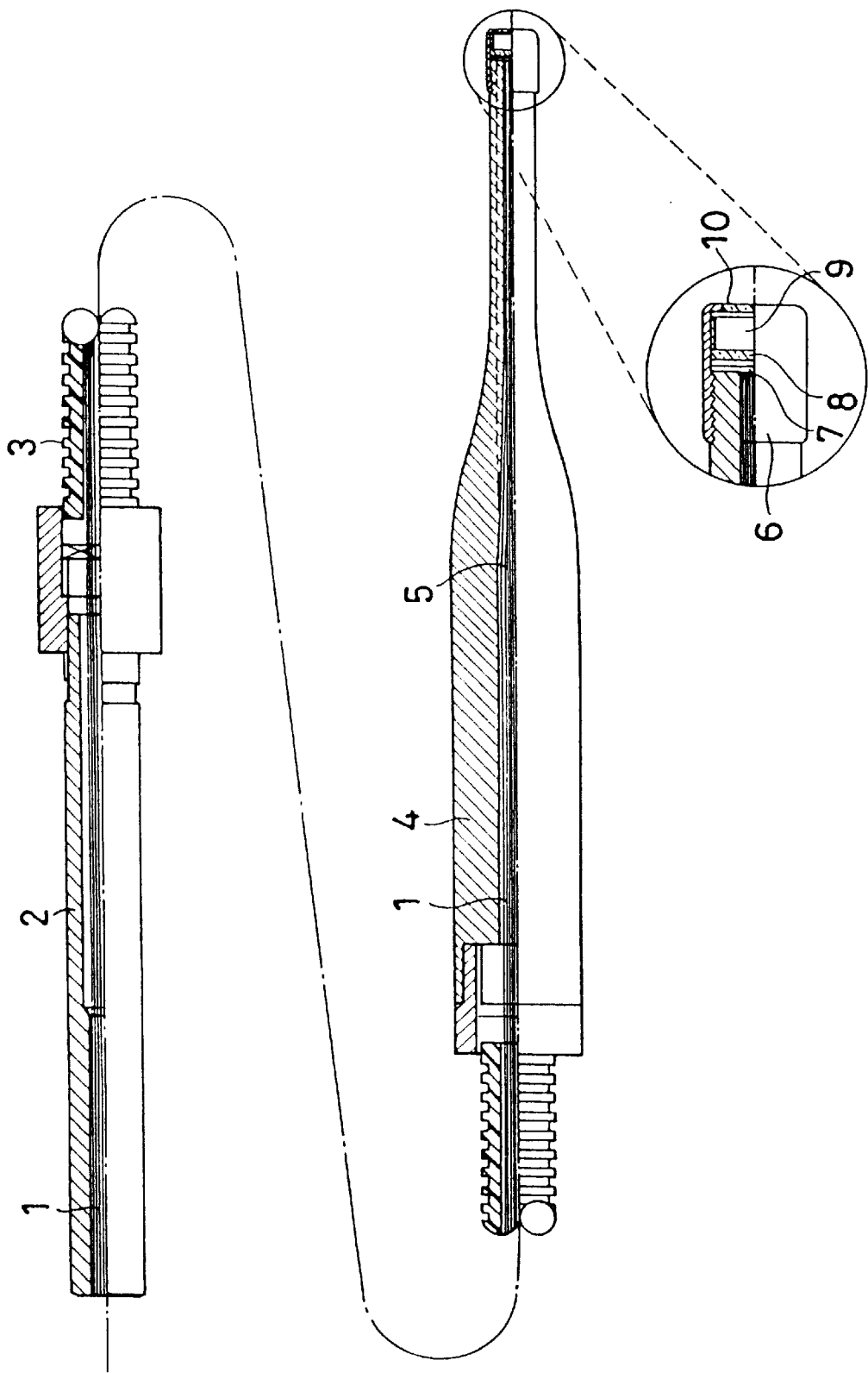
FIG. 1 is a side elevational view showing the upper cross-section of an optical fiber unit for medical examination and treatment according to a first preferred embodiment of the invention.

FIG. 1 is a side elevational view showing the upper cross-section of major parts of an optical fiber unit for medical examination and treatment according to the first preferred embodiment of the invention. The principal part of the optical fiber unit for medical examination and treatment according to the preferred embodiment consists of optical fiber light guide 1, protection pipe 2, flexible guide tube 3, probe 4, tapered conduit part 5 and tip end cap 6.

The optical fiber light guide 1 is of a quartz-oriented multi-constituent structure in which about 19,000 optical fibers consisting of cores having different refraction indexes and clad are bundled while the diameter of each single fiber is 50 $\mu$m or so. Furthermore, optical fiber light guide 1 does not allow any transmission of infrared rays of long wavelength band of 1.6 $\mu$m or more.

The protection pipe 2 is a pipe made of aluminum, etc., which protects the base part of optical fiber light guide 1.

The flexible guide tube 3 has an optical fiber light guide 1 inserted thereinto and is to protect the same by its surrounding so that optical fiber light guide does not bend beyond a certain limit.

The probe 4 is fixed at the tip end part of the optical fiber light guide 1 and is a part which is operated by being nipped by fingers or an arm device. The diameter of probe 4 is gradually made smaller toward the tip end side thereof in line with the tapered conduit part 5, wherein a male screw onto which a tip end cap 6 is screwed is threaded on the outer circumference of the tip end part.

The tapered conduit part 5 is a hard part formed to be gradually made smaller toward the tip end part thereof by heating and elongating the tip end part of optical fiber light guide 1. The tapered conduit part 5 takes a role of condensing light emitted from the tip end plane of optical fiber light guide 1 to a light flux having a circular cross-section, which is approximate to a parallel light flux.

The tip end cap 6 is constructed so as to be detachably screwed into the tip end part of probe 4, and a female screw which is screwed into the tip end part of probe 4 is threaded on the interior thereof, wherein spring 7, rectilinear polarization plate 8, sleeve 9 and cover glass 10 are disposed one after another.

The rectilinear polarization plate 8 is formed so that film-like polyvinyl alcohol is dyed with an iodine solution and is sandwiched by optical glass plates at both the inside and outside thereof, and the same takes a role of straightening the light polarization plane of a wavelength band of 0.6 to 1.6 $\mu$m or the like. Furthermore, it has been already known that rectilinearly polarized infrared rays have remarkable effects in activating biopolymers and improving minute circulations and further increase the curing effects.

Next, a description is given of actions of an optical fiber unit for medical examination and treatment according to the preferred embodiment constructed as described above.

Light including infrared rays emitted from a light source (not illustrated) is made incident into the base end plane of optical fiber light guide 1.

The optical fiber light guide 1 cuts off the infrared rays of a long wavelength band of 1.6 $\mu$m or more and may allow light of other wavelength bands to pass therethrough. The passed light reaches the tip end side while being reflected by clad in the cores of the respective optical fibers, is gradually condensed at the tapered conduit part 5 and is caused to outgo through the tip end plane.

Light including infrared rays emitted from the tip end plane of the optical fiber light guide 1 is rectilinearly polarized by a rectilinear polarization plate 8 and is irradiated onto an affected part through a cover glass 10.

At this time, since the optical fiber light guide 1 has flexibility and is made bendable, the infrared rays can be condensed and irradiated to be spot-like onto an affected part at any position at a high energy concentration by operating the probe 4.

Light irradiated by an optical fiber unit for medical examination and treatment onto an affected part has a ratio in which visible light rays which can be seen to be red occupy about 5% and the invisible near infrared rays which can be absorbed deeply into a human body and gives an effect of heating occupy about 95%. The peak of concentration exists in the vicinity of 1.0 $\mu$m. Light of a wavelength band of 0.6 to 1.6 $\mu$m or so has a great biopenetration power by which the deep part of the living can be heated and activated.

Therefore, an optical fiber unit for medical examination and treatment has effects in the indications described below;

(1) Pain

Subacute and chronic pains and neuralgia of muscles and joints (i) Neck . . . Pain of cervical vertebra, whiplash injury, crick in sleep (ii) Shoulder, back . . . Scalpulohumeral periarthritis, dorsum pain, shoulder joint sprain (iii) Lumbar region . . . Slipped disk, sciatica, pain due to hernia of intervertebral disk (iv) Arm . . . Elbow joint pain, tennis elbow, pollex snapping fingers (v) Leg . . . Knee joint pain (2) Inflammatory pain, lesion (after the acute term)

Pains resulting from sprain, fracture, tendosynovitis, slipped disk, deep muscle injury, ligament injury, and spasm suppression of muscles (3) Arthritis and Rheumatism Rheumatic arthritis, ostarthritis deformans (excluding the acute, subacute ostarthritis)

(4) Dermatose

Chronic dermatitis, acnevulgaris, bedsore

Figure 2:
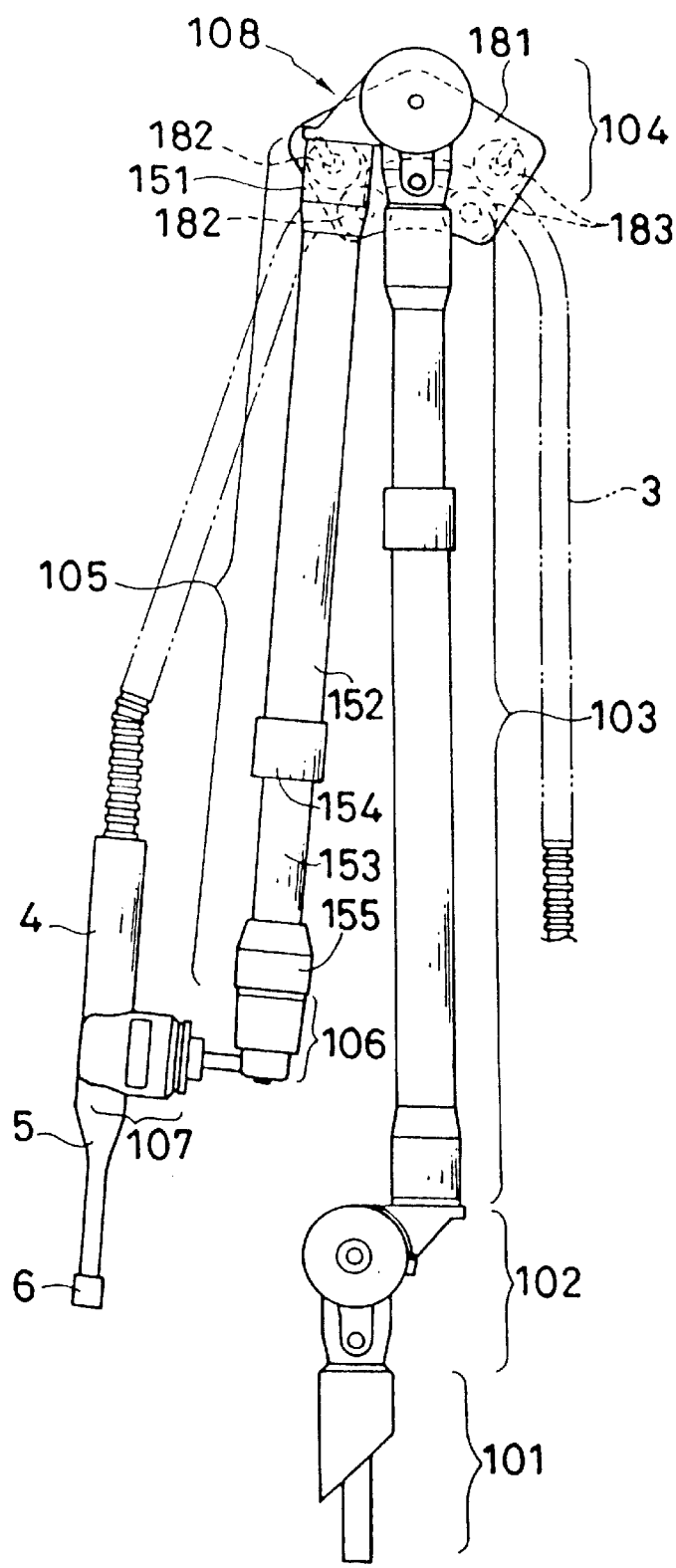
FIG. 2 is a front elevational view showing an arm device for optical fiber according to the first preferred embodiment of the invention.

FIG. 2 is a front elevational view showing a state where an optical fiber unit for medical examination and treatment according to the abovementioned preferred embodiment is attached to an arm device for optical fiber according to one preferred embodiment of the invention. The major part of the arm device for optical fiber according to the preferred embodiment consists of a base end part 101, a first joint part 102, a first extendable arm part 103, a second joint part 104, a second extendable arm part 105, a third joint part 106, and a probe retaining part 107.

Figure 4:
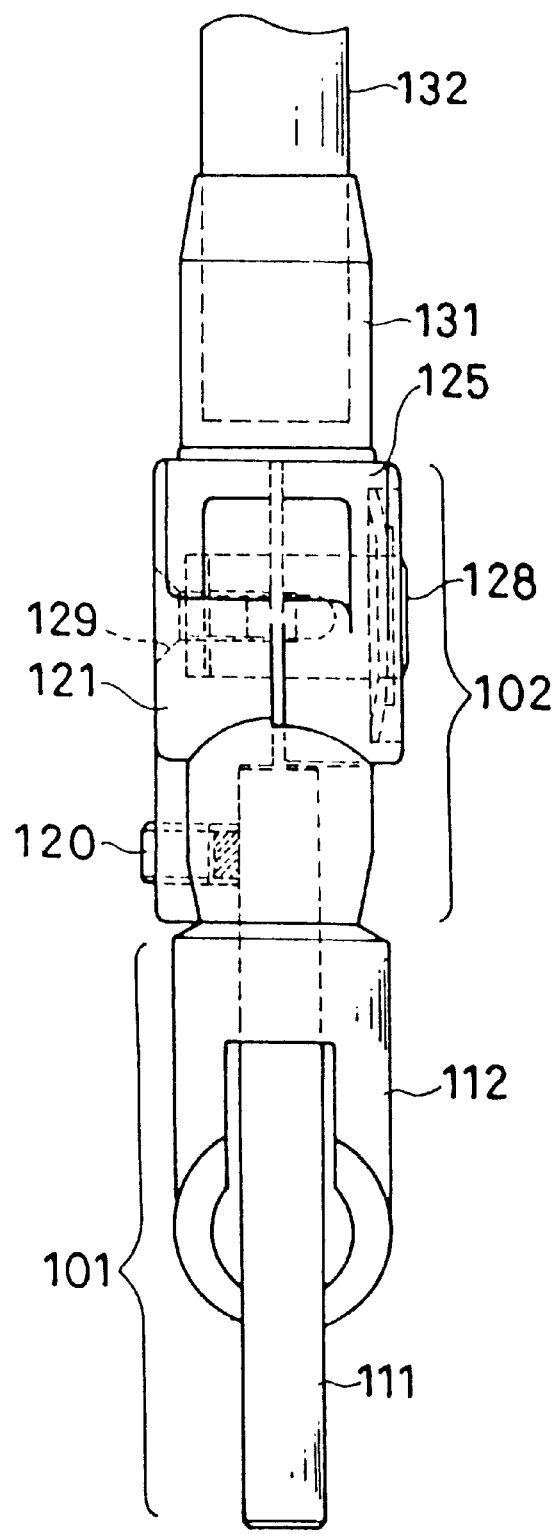
FIG. 4 is an enlarged view of the base part and first joint part illustrated in FIG. 2.

The base end part 101 is, as shown in enlargement in FIG. 4, composed of a shaft 111 inserted into and fixed at a light source device main body (not illustrated) of an optical fiber unit for medical examination and treatment and a cylindrical member 112 into which the shaft 111 is internally inserted. The lower end plane of the cylindrical member 112 is diagonally notched and is fixed at the outward diagonal plane of the light source device main body so as not to be rotatable.

Figure 5:
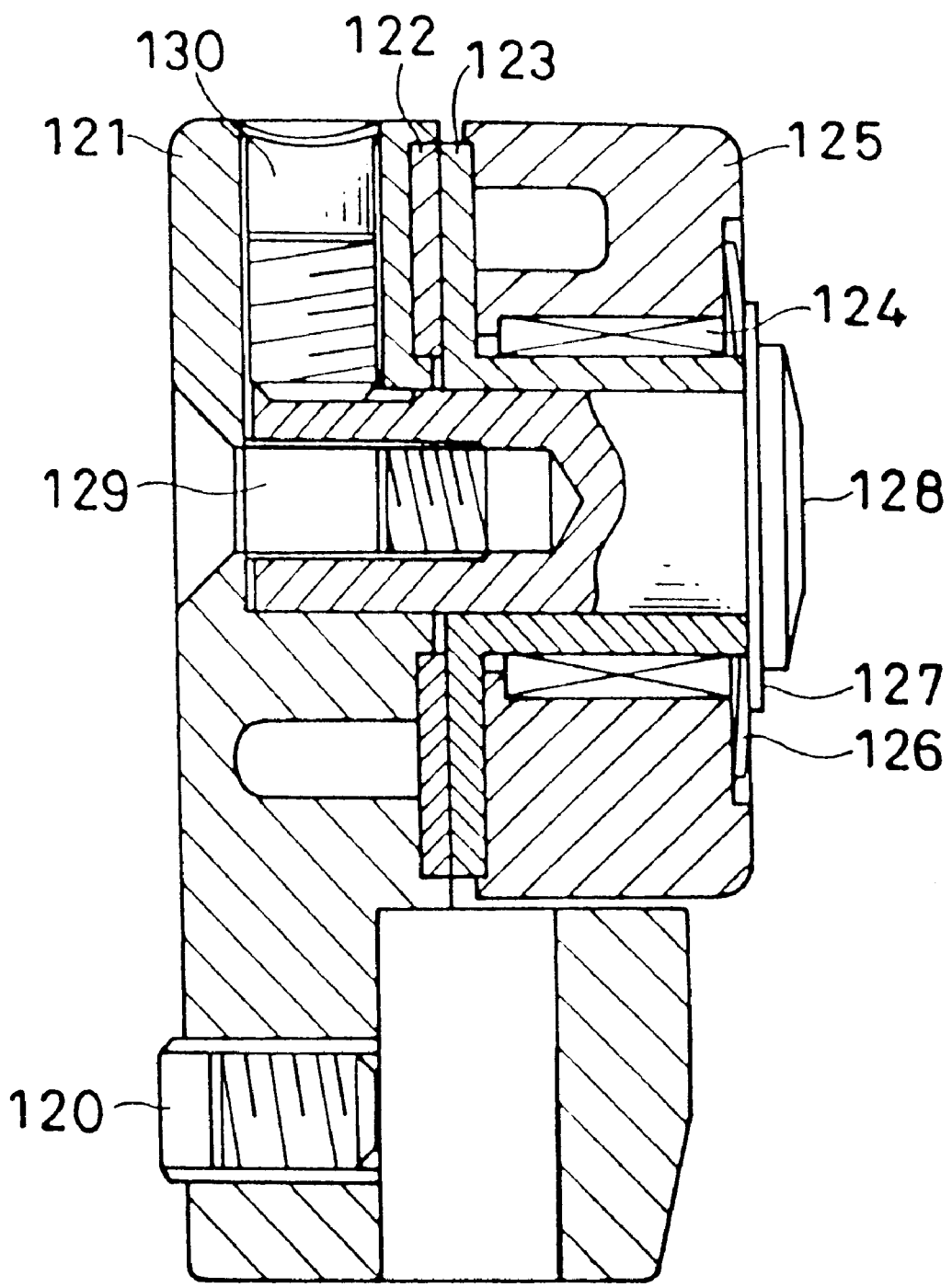
FIG. 5 is a cross-sectional view of the first joint part illustrated in FIG. 2.

The first joint part 102 is, as shown in cross-section in FIG. 5, composed of an axial fixing member 121 rotatably attached by a screw 120 via a shock absorbing member fitted into the shaft 111 of the base end part 101 so as to be prevented from slipping off, a bearing member 125 rotatably attached to the axial fixing member 121 via a brake shoe 122, an intermediate member 123 and a one-way clutch 124, an axis 128 inserted into the bearing member 125 and screwed by a screw 129 at the axial fixing member 121 via a plate spring 126 and a washer 127, a screw 130 screwed into the axial fixing member 121 so as to regulate the rotations of the axis 128. With such a construction, it is possible for the axial fixing member 121 to turn 360 degrees on the horizontal plane centering around the shaft 111 and possible for the bearing member 125 to turn about 100 degrees on the perpendicular plane with respect to the axial fixing member 121. Furthermore, the first extendable arm part 103 is locked by the one-way clutch 124 in the direction along which the first extendable arm part 103 falls down, whereby no load is given in the direction of vertically returning the first extendable arm part 103.

Figure 3:
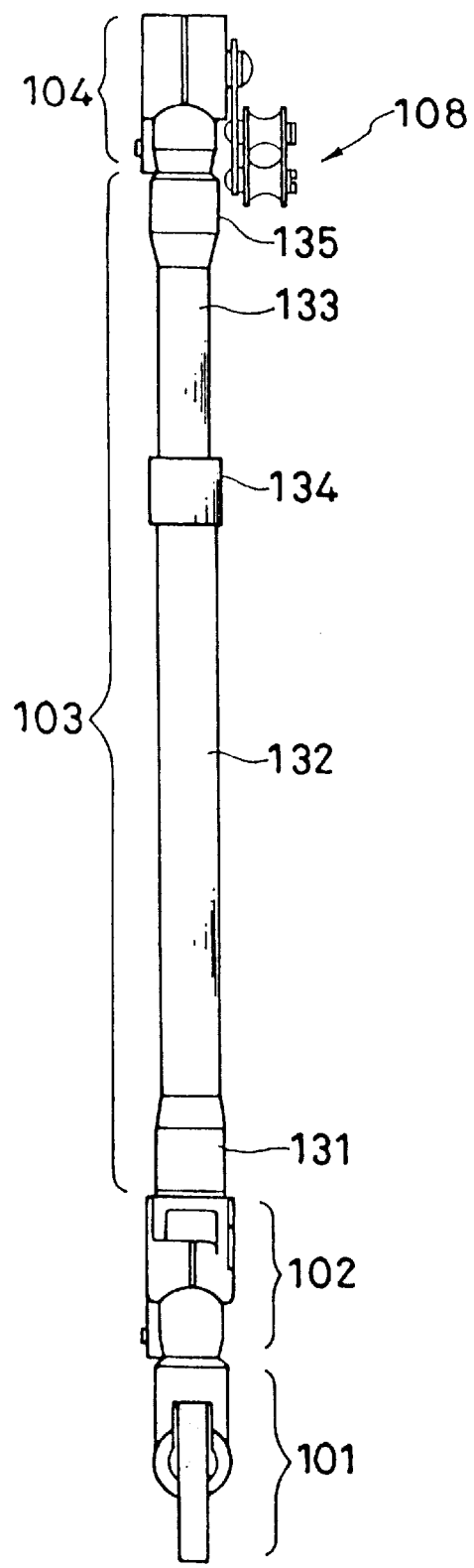
FIG. 3 is a side elevational view of an arm device for optical fiber according to the preferred embodiment.

As shown in FIG. 3, the first extendable arm part 103 is composed of a lower cover 131 fixed at the bearing member 125 of the first joint part 102, an outer pipe 132, the lower end of which is inserted into and fixed in the lower cover 131, an inner pipe 133 which is internally inserted into the outer pipe 132, a locking member 134 secured on the upper end of the outer pipe 132, and an upper cover 135 fixed at the second joint part 104, into which the upper end of the inner pipe 133 is inserted and fixed. By operating the locking member 134, the outer pipe 132 is fixed with respect to the inner pipe 133 and the first extendable arm part 103 can be set to any desired length.

Figure 6:
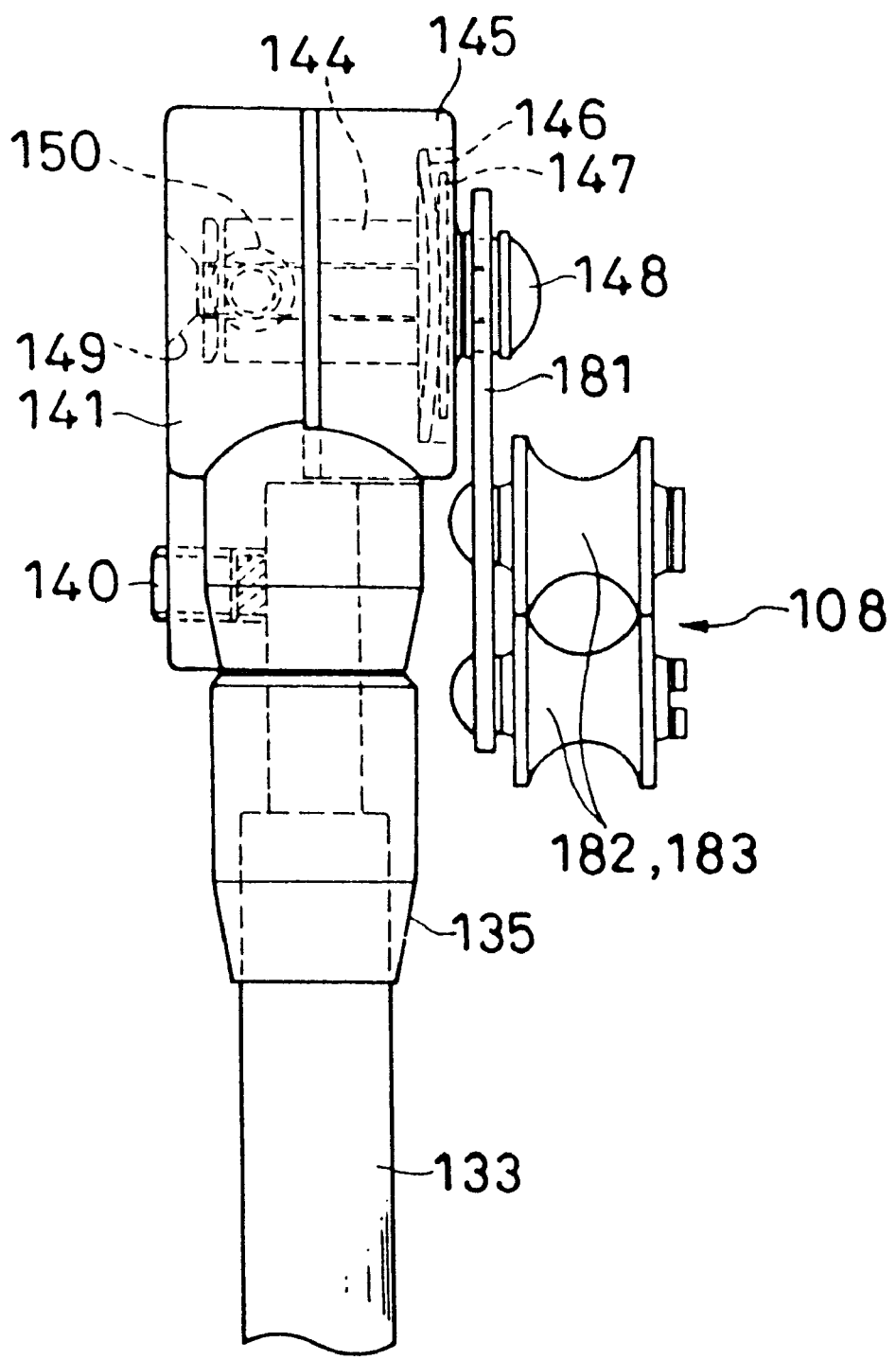
FIG. 6 is an enlarged side elevational view of the second joint part illustrated in FIG. 2.

As shown in enlargement in FIG. 6, the second joint part 104 is constructed almost equivalent to the first joint part 102. That is, the second joint part 104 is composed of an axial fixing member 141 fitted into the shaft of the first extendable arm part 103 and rotatably attached by a screw 140 via a shock absorbing member so as to be prevented from slipping off, a bearing member 145 rotatably attached to the axial fixing member 141 via a one-way clutch 144, an axis 148 inserted into the bearing member 145 and screwed by a screw 149 to the axial fixing member 141 via a plate spring 148 and a washer 147, and a screw 150 screwed into the axial fixing member 141 so as to regulate the rotations of the axis 148. With such a construction, the axial fixing member 141 can be turned 360 degrees centering around the shaft of the first extendable arm part 103 and simultaneously can be turned about 100 degrees in the perpendicular plane with respect to the plane of rotation. Furthermore, the second extendable arm part 105 is locked by the one-way clutch 144 in the direction along which the second extendable arm part 105 falls down, whereby no load is given when moving the second flexible arm part 105 in the horizontal direction.

Furthermore, as shown in FIG. 3 and FIG. 6, a guide part 108 in which a flexible guide tube 3 of an optical fiber unit for medical examination and treatment is insertably put is secured at a side of the second joint part 104. The guide part 108 is composed of a fan-shaped plate 181 fixed at the axis 148 of the second joint part 104 and two sets of roller pairs 182, 183 attached to the fan-shaped plate 181 (See FIG. 2).

The second extendable arm part 105 is constructed almost equivalent to the first extendable arm part 103. That is, as shown in FIG. 2, the second extendable arm part 105 consists of an upper cover 151 fixed at the bearing member 145 of the second joint part 104, an outer pipe 152, the upper end of which is attached to the upper cover 151, an inner pipe 153 internally inserted into the outer pipe 152, a locking member 154 secured at the lower end of the outer pipe 152, and a lower cover 155 fixed at the third joint part 106, into which the lower end of the inner pipe 153 is inserted and fixed. By operating the locking member 154, the outer pipe 152 is fixed at the inner pipe 153 and the second extendable arm part 105 can be set to any desired length.

Figure 7:
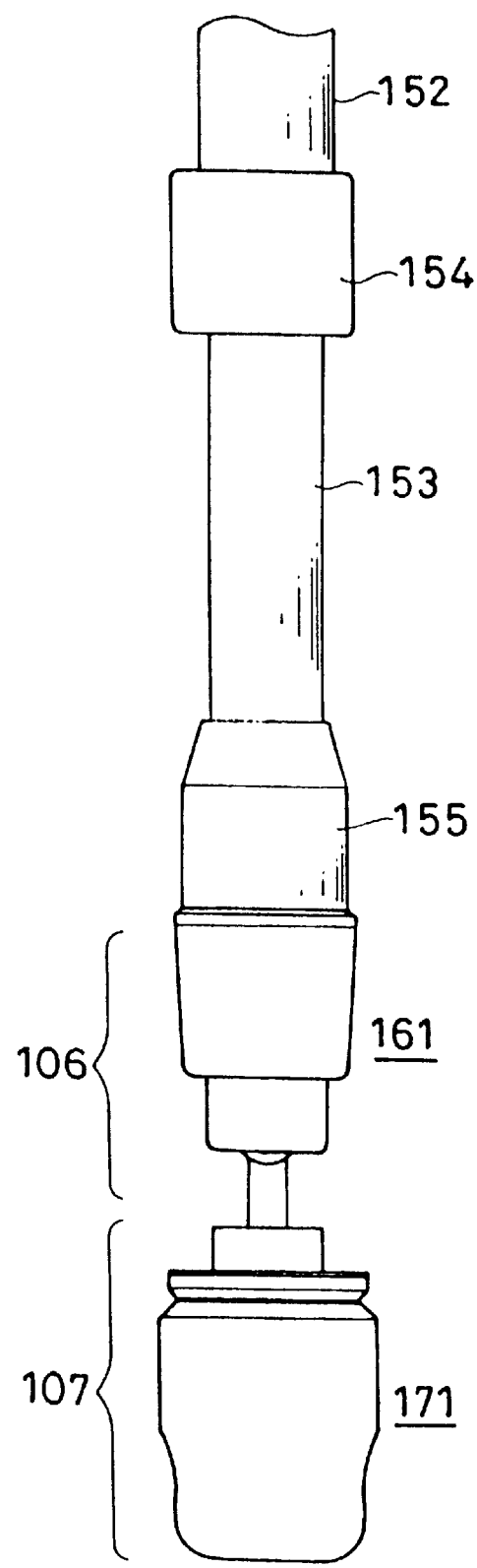
FIG. 7 is an enlarged side elevational view of the third joint part and probe retaining part illustrated in FIG. 2.
Figure 8:
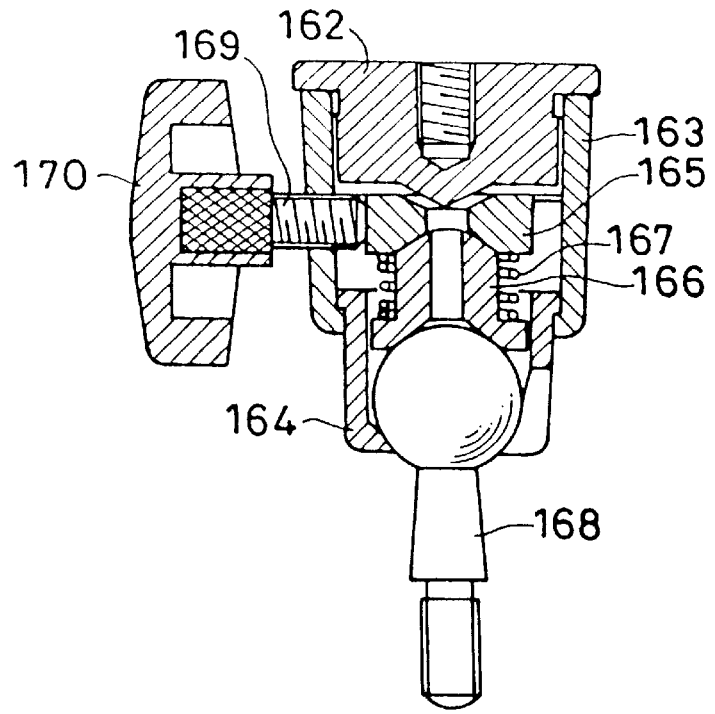
FIG. 8 is an enlarged cross-sectional view of the third joint part illustrated in FIG. 2.

As shown in enlargement in FIG. 7, the third joint part 106 is composed of a universal joint base 161 attached to the second extendable arm part 105. The universal joint base 161 is, as shown in cross-section in FIG. 8, composed of a base 162 which is provided with a threaded hole to be fixed at the lower cover 155 of the second extendable arm part 105, a first cylindrical member 163 which surrounds the base 162, a second cylindrical member 164 slidably fitted with respect to the first cylindrical member 163 so as to be prevented from slipping off, a tapered member 165 secured in the first cylindrical member 163, a sliding member 166 which slides in line with movements of the tapered member 165, a coil spring 167 which intervenes between the taper member 165 and the sliding member 166, a universal joint member 168, the position of which is fixed in the second cylindrical member 164 by being pressed by the sliding member 166, a fixing screw 169 which is screwed into the first cylindrical member 163 to press and move the tapered member 165, and a knob 170 attached to the fixing screw 169. With such a construction, as the fixing screw 169 is screwed by operating the knob 170 after operating the universal joint member 168 in a desired direction, the tapered member 165 moves to cause the sliding member 166 to slide against the resiliency of the coil spring 167, whereby the universal joint member 168 is pressed and fixed in the second cylindrical member 164.

Figure 9:
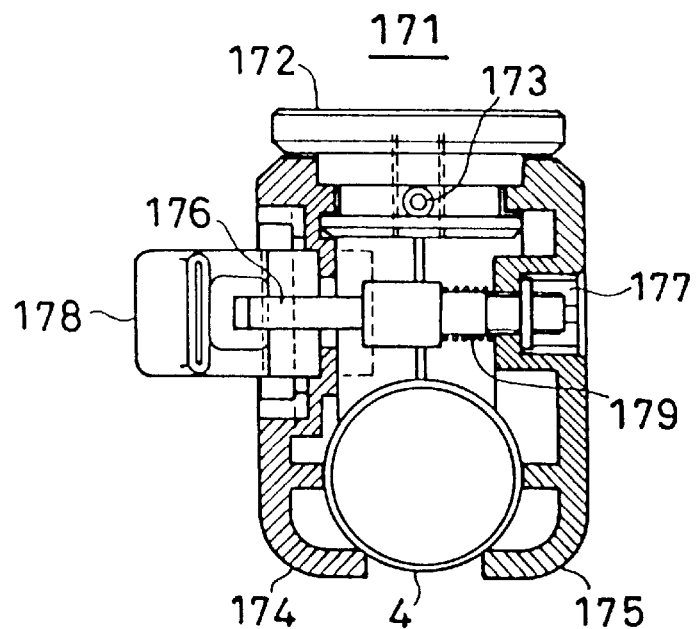
FIG. 9 is an enlarged side elevational view of the probe retaining part illustrated in FIG. 2.

As shown in enlargement in FIG. 7, the probe retaining part 107 is composed of a gripping part 171 attached to the universal joint base 161. The gripping part 171 is, as shown in cross-section in FIG. 9, composed of a base 172 screwed to the tip end of the universal joint member 168 of the universal joint base 161, a fixing screw 173 by which the base 172 is fixed at the universal joint member 168, a pair of gripping members 174, 175 attached to the base 172, a sliding axis 176 secured so as to pass through the pair of gripping members 174, 175, a nut 177 which fixes one end of the sliding axis 176, a knob 178 attached to the other end of the sliding axis 176, and a coil spring 179 which presses the sliding axis 176. With such a construction, the probe 4 of an optical fiber unit for medical examination and treatment is inserted between the gripping members 174, 175 with the gripping members 174, 175 slackened by operating the knob 178. Thereafter, by operating the knob 178, the sliding axis 176 is caused to move against the coil spring 179, thereby causing the clearance between the gripping members 174, 175 to be made narrow. Therefore, the probe 4 is retained at the gripping part 171. Furthermore, the probe retaining part 107 can be turned 360 degrees with respect to the center of the universal joint base 161 and can be inclined about 120 degrees.

Next, a description is given of how to use an arm device for optical fiber according to the preferred embodiment constructed as described above.

First, a user of an optical fiber unit for medical examination and treatment inserts the shaft 111 of the base end part 101 into its fixing hole (not illustrated) drilled at the light source device main body and attaches an arm device for optical fiber to the light source device main body. Next, a flexible guide tube 3 of the optical fiber unit for medical examination and treatment, which is taken out from the light source device main body, is inserted into two sets of roller pairs 182, 183 of the guide part 108 attached to the second joint part 104. Furthermore, the probe 4 of the optical fiber unit for medical examination and treatment is inserted between the gripping members 174, 175 of the probe retaining part 107, wherein by operating the knob 178, the probe 4 of the optical fiber unit is retained between the gripping members 174, 175. With the above procedures, the optical fiber unit for medical examination and treatment can be attached to the arm device for optical fiber.

From this state, the user of the optical fiber unit for medical examination and treatment loosens the locking member 134 of the first extendable arm part 103 once, and fixes the locking member 134 after pulling out the inner pipe 133 from the outer pipe 132 and inserting the same thereinto, whereby he is able to set the first extendable arm part 103 to any desired length. Furthermore, the second extendable arm part 105 can be set to any desired length. Since the extendable guide tube 3 is insertably nipped between two sets of roller pairs 182, 183 of the guide part 108, the extendable guide tube 3 can move, following the elongation and contraction of the first extendable arm part 103 and the second extendable arm part 105 even though the first extendable arm part 103 and the second extendable arm part 105 are contracted and elongated with the probe 104 retained in the probe retaining part 107.

Next, when the user of the optical fiber unit for medical examination and treatment holds the probe 4 and moves the same horizontally, the second joint part 104 will be rotated in the direction opposite the locking direction of one-way clutch to cause the second flexible arm part 105 to rise in the horizontal direction with a comparatively weak force and to move to any desired position. Accordingly, since the second joint part 104 is locked by the one-way clutch 144 if his hand is released at the position where the second extendable arm part 105 moved, the second extendable arm part 105 retains its stopped position against its gravity, whereby the probe 4 can be retained with its position kept.

In a case where a user of the optical fiber unit for medical examination and treatment moves the first extendable arm part 103 in the horizontal direction so as to make the same fall down, since a locking force is actuated onto the first joint part 102 by the one-way clutch 124, it is necessary to move the first extendable arm part 103 with a comparatively strong force. However, it is possible to keep the posture of the first extendable arm part at the position where the same has been pressed and moved.

Furthermore, if a force in the rotation direction is given to the first extendable arm part 103 at an optional posture of the first extendable arm part 103, it is possible for the first extendable arm part 103 to turn 360 degrees centering around the shaft 111 of the base end part 101 along with the first joint part 102. Similarly, if a force in the rotation direction is given to the second extendable arm part 105 at an optional posture of the second extendable arm part 105, it is possible for the second extendable arm part 105 to turn 360 degrees centering around the shaft of the first extendable arm part 103 along with the second joint part 103.

Therefore, since the optical fiber unit for medical examination and treatment can be easily operated, following the arm device for optical fiber, the user can comparatively easily allow the probe 4 to come near an affected part.

On the other hand, in a case where the optical fiber unit for medical examination and treatment and arm device for optical fiber are reset to their initial position shown in FIG. 2 after the optical fiber unit is used, first the user of the optical fiber unit holds the probe 4 in his hand and moves the same so as to come near the base end part 101, wherein the second joint part 104 can turn against the locking by the one-way clutch 144, the angle between the second extendable arm part 105 and the first extendable arm part 103 is made narrow, and it is possible to reset the second flexible arm part 105 to such a state where the second extendable flexible arm part 105 is approached to the first extendable flexible arm part 103.

Next, if a force is given to the first extendable arm part 103 in its erecting direction, the first extendable arm part 103 can be reset to the erecting position with a comparatively weak force, wherein the optical fiber unit for medical examination and treatment and arm device for optical fiber can be reset to the initial positions shown in FIG. 2.

Figure 10:
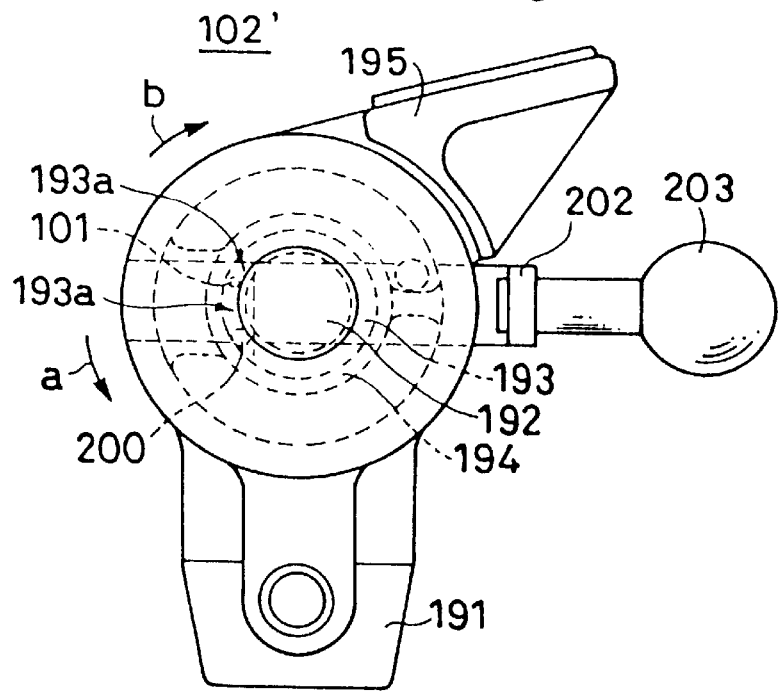
FIG. 10 is an enlarged side elevational view showing a modified example of the first joint part illustrated in FIG. 2.
Figure 11:
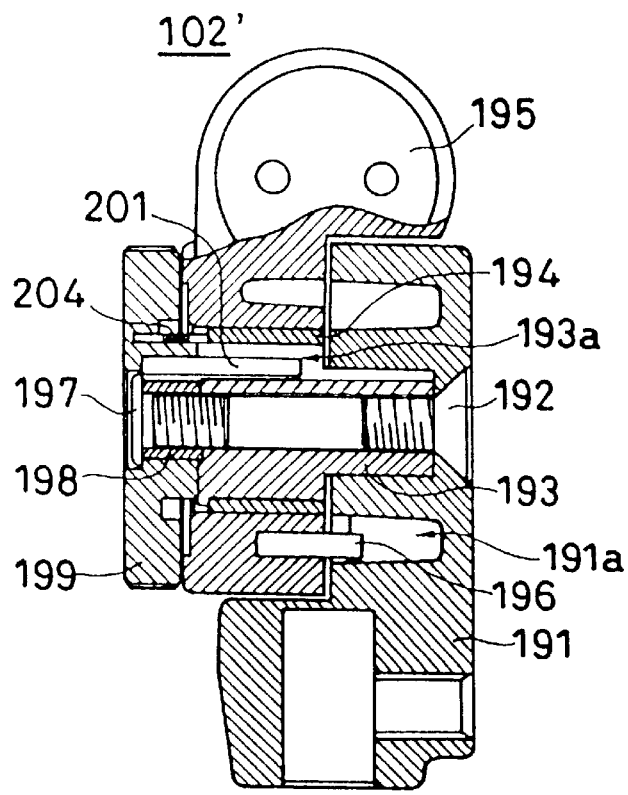
FIG. 11 is a cross-sectional view of a modified example of the first joint part illustrated in FIG. 10.

FIG. 10 and FIG. 11 are respectively a side elevational view and a cross-sectional view each showing a construction of a first joint part 102' which is a modified example of the first joint part 102 shown in FIG. 2 and FIG. 5. The first joint part 102' of this example is composed of an axial fixing member 191 rotatably attached to the shaft 111 of the base end part 101, a hollow shaft 193, attached to the axial fixing member 191 via a screw 192, having a notch 193a for one-way clutch on its side circumferential surface, a bearing member 195 rotatably fitted to the hollow shaft 193 via a sintered ring 194, an angle regulating pin 196 implanted in the bearing member 195 and inserted into an arcuate groove 191a of the axial fixing member 191, a rotating plate member 199 rotatably attached to the hollow shaft 193 by a screw 197 and fixed via a sintered ring 198, a roller 200 for one-way clutch, which is idly fitted into the notch 193a, a lock cancelling pin 201 implanted in the rotating plate member 199 for cancelling the locking of the one-way clutch in engagement with the roller 200, an arm 202 fixed at the rotating plate member 199, a ball knob 203 attached to the arm 202, and a reset spring 204 for resetting the rotating plate member 199 to the initial position.

The first joint part 102' of this example, which is constructed as described above, is such that the locking effected by the one-way clutch consisting of the notch 193a of the hollow shaft 193 and the roller 200 can be manually cancelled by providing the same with a ball knob 203. That is, although the bearing member 195 can be rotated without any load when the same is rotated in the direction of arrow "a", the roller 200 is engaged in the notch 193a to effect the locking if the bearing member 195 is attempted to rotate in the direction of arrow "b". When the ball knob 203 is pushed up from this locked state, the lock cancelling pin 201 is engaged with the roller 200 via the arm 202 and rotating plate member 199, thereby cancelling the engagement of the roller 200 with the notch 193a of the hollow shaft 193, wherein the lock comes off. Therefore, since both the axial fixing member 191 and the bearing member 195 are made free, it is possible to comparatively easily shift down the first extendable arm part 103 to any desired inclination position. And if your hand is released from the ball knob 203 at a position where the first extendable arm part 103 is inclined, the rotating plate member 199 is reset by a restoration resiliency of the reset spring 104 to cause the roller 200 to be again engaged in the notch 193*a* and to cause the one-way clutch to be locked again. Furthermore, in a case where the first extendable arm part 103 is reset to the initial erect position, since the lock of the one-way clutch does not operate, it is possible to reset the first extendable arm part 103 to the erect position with a comparatively weak force.

Furthermore, an arm device for optical fiber according to the abovementioned preferred embodiment is described on the basis of the example in which an optical fiber unit for medical examination and treatment shown in FIG. 1 is attached thereto. An optical fiber unit attached to the arm device for optical fiber is not necessarily limited to that for medical examination and treatment. Various kinds of optical fiber units for industrial applications, medical diagnosis, etc. may be attached thereto for use.

What is claimed is:

1. A combination of an arm device and an optical fiber, comprising:

a base end part fixed at a light source device main body;

a first joint part which is rotatably centered around a shaft of said base end part, and is attached to be rockable in one direction via a one-way clutch in the plane perpendicular to the rotation plane;

a first extendable arm part extendably attached to said first joint part;

a second joint part which is rotatably centered around a shaft of said first extendable arm part, and is attached to be rockable in one direction via a one-way clutch in the plane perpendicular to the rotation plane;

a guide part mounted on said second joint part for guiding the optical fiber;

a second extendable arm part extendably attached to said second joint part;

a third joint part rotatably and rockably attached to said second extendable arm part; and a probe retaining part attached to said third joint part for retaining a probe for receiving light from said optical fiber.

2. A combination of an arm device and an optical fiber as set forth in claim 1, wherein said first joint part has an operating member for cancelling a locking of said one-way clutch.

3. A combination of an arm device and an optical fiber as set forth in claim 1, wherein said second joint part has a guide part which insertably nips a flexible guide tube for the optical fiber.

\* \* \* \* \*